United States Patent [19]

Glover et al.

[11] Patent Number: 4,590,558
[45] Date of Patent: May 20, 1986

[54] METHOD AND APPARATUS FOR REMOVING OBJECTS FROM CT IMAGES

[75] Inventors: Gary H. Glover, Waukesha; Norbert J. Pelc, Wauwatosa, both of Wis.

[73] Assignee: General Electric Company, Waukesha, Wis.

[21] Appl. No.: 335,973

[22] Filed: Dec. 30, 1981

[51] Int. Cl.⁴ .................... G06F 15/42; G06K 9/40
[52] U.S. Cl. .................... 364/414; 358/111; 364/521; 364/571; 378/901; 382/54
[58] Field of Search ............ 340/707, 709, 723, 728, 340/747; 358/111, 112, 113, 183; 364/413–415, 521, 571; 382/6, 16, 22, 54; 378/901

[56] References Cited

U.S. PATENT DOCUMENTS

| | | | |
|---|---|---|---|
| 4,017,680 | 4/1977 | Anderson et al. | 358/183 X |
| 4,075,700 | 2/1978 | Blay | 364/413 X |
| 4,149,081 | 4/1979 | Seppi | 382/6 X |
| 4,223,384 | 9/1980 | Hounsfield et al. | 364/414 |
| 4,231,097 | 10/1980 | Shibayama et al. | 364/414 X |
| 4,245,244 | 1/1981 | Lijewski et al. | 358/111 |
| 4,259,725 | 3/1981 | Andrews et al. | 364/521 |
| 4,272,820 | 6/1981 | Lux | 364/414 |
| 4,323,974 | 4/1982 | Sekigawa | 382/54 X |
| 4,345,313 | 8/1982 | Knox | 340/709 X |
| 4,356,555 | 10/1982 | Ejiri et al. | 382/54 X |
| 4,360,883 | 11/1982 | Ejiri et al. | 382/54 X |

Primary Examiner—Errol A. Krass
Assistant Examiner—Kevin J. Teska
Attorney, Agent, or Firm—Leydig, Voit & Mayer, Ltd.

[57] ABSTRACT

Method and apparatus for producing CT images in which localized regions ("rub-out" regions) of the original object are not reproduced in order to eliminate artifacts generated by objects within those regions. An operator defines a rub-out region encompassing the object to be removed. The projection set is then modified by creating an average function within the rub-out region which is strongly influenced by the discontinuity created by the object. That information is then utilized to modify the projection set, in effect eliminating the object from the set. The projection set is then used to create a reconstructed image in the normal way.

5 Claims, 8 Drawing Figures

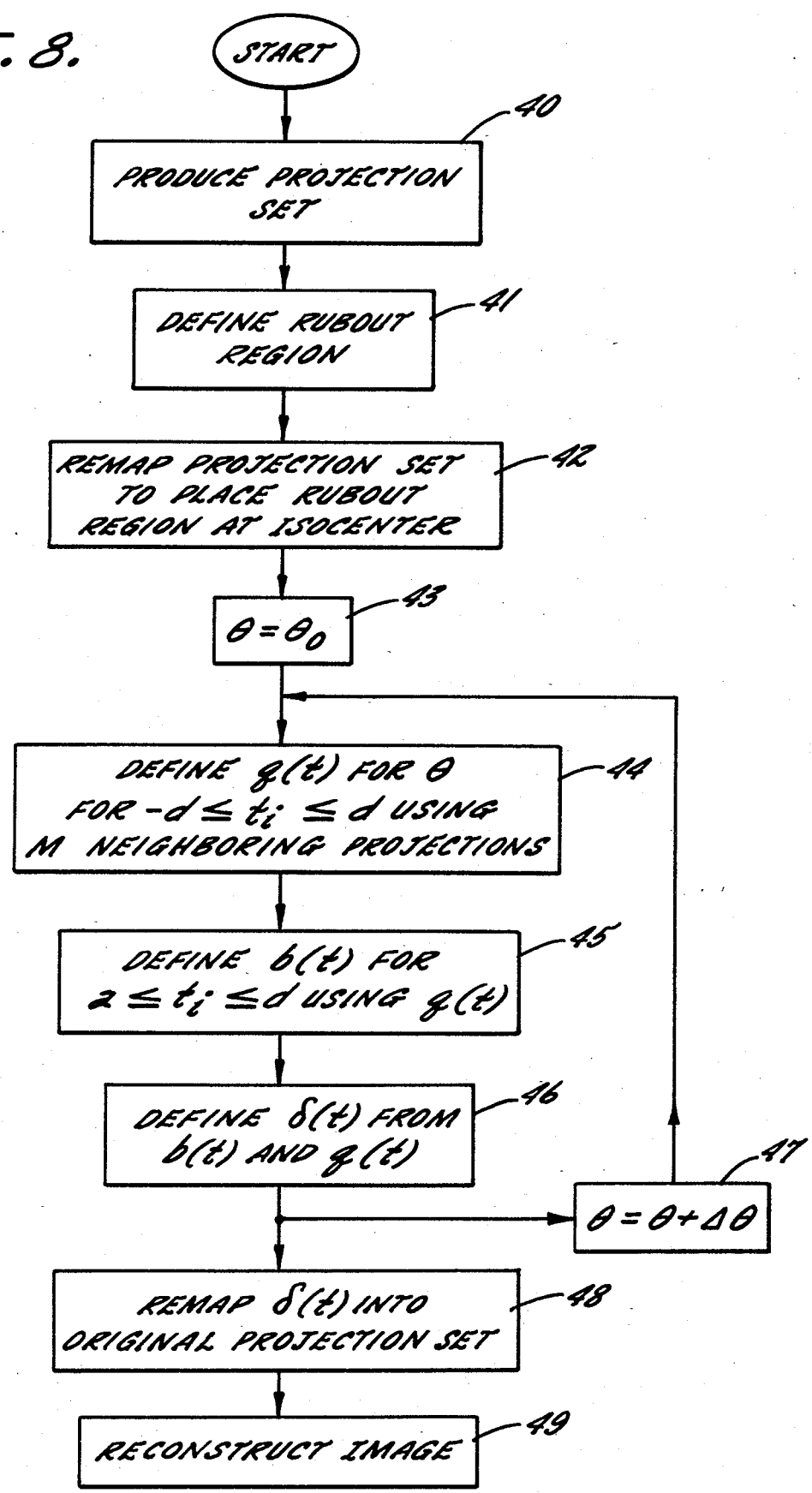

METHOD AND APPARATUS FOR REMOVING OBJECTS FROM CT IMAGES

BACKGROUND OF THE INVENTION

This invention relates to computed tomography and more particularly to a method and apparatus for removing artifacts from CT images.

Modern computed tomography has provided diagnostic images containing information which was simply not available or difficult to interpret using prior imaging techniques. At the same time, structures in or on the body which had previously not created serious imaging problem have led to artifacts which made CT images difficult to interpret.

One example is that of surgical clips within the slice to be imaged. Such clips are typically of very high density as compared to the surrounding tissue and are often found to create artifacts known as "starburst". Such artifacts limit the diagnostic utility of the CT image. The starburst artifact caused by surgical clips is characteristic of a class of artifacts created by areas within the slice exhibiting sharp but localized density discontinuities.

SUMMARY OF THE INVENTION

In view of the foregoing, it is a general aim of the present invention to improve the quality of this class of CT images by minimizing the effect of image artifacts created by sharp localized discontinuities.

More particularly, an object of the present invention is to reduce artifacts caused by sharp localized discontinuties like surgical clips without degrading the CT image by introducing other artifacts.

Other objects and advantages will become apparent from the following detailed description when taken in conjunction with the drawings in which:

BRIEF DESCRIPTION OF THE DRAWINGS

FIG. 8 is a flow chart characteristic of the present invention.

DESCRIPTION OF THE PREFERRED EMBODIMENT

While the invention will be described in connection with a preferred embodiment, there is no intent to limit it to that embodiment. On the contrary, the intent is to cover all alternatives, modifications and equivalents included within the spirit and scope of the invention as defined by the appended claims.

Figure 1:
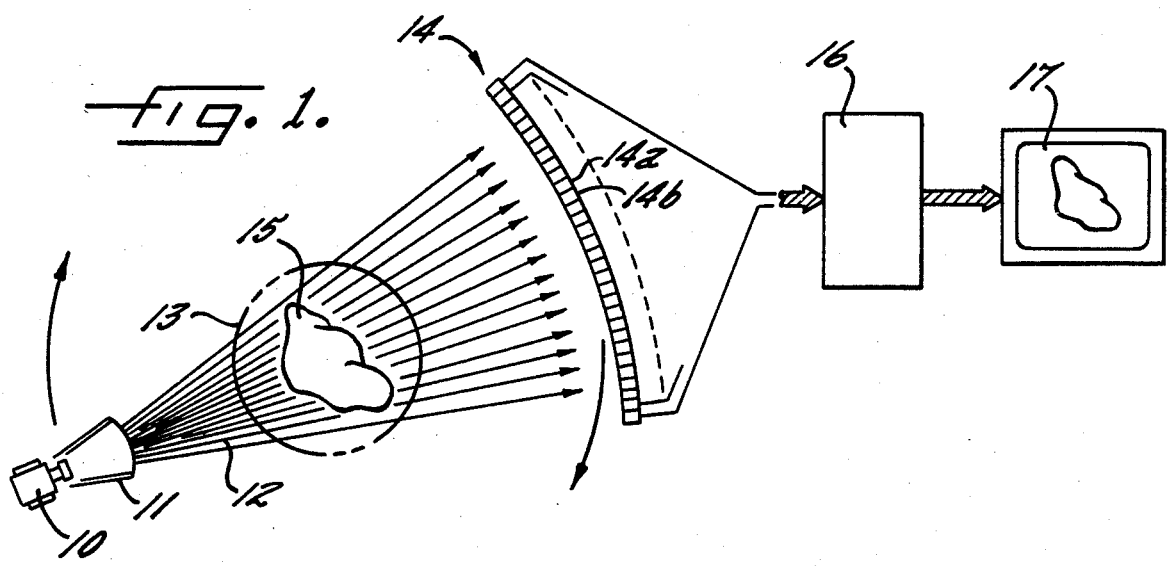
FIG. 1 is a schematic view illustrating the major elements of a CT scanner.

Turning now to the drawings, FIG. 1 schematically illustrates the major elements of a CT scanner. The scanner includes a source of penetrating radiation 10, very often in the form of a rotating anode x-ray tube. The radiation produced by the x-ray tube 10 is collimated at 11 to produce a thin fan beam of radiation 12 which is projected through a patient aperture 13 toward an x-ray detector array 14. A body to be examined, such as a patient 15, is positioned within the patient aperture 13 in the path of the fan beam of x-rays 12 such that the beam passing through the body is attenuated in dependence on the density of the objects encountered. As a result, each detector cell 14a, 14b, etc. produces an electrical signal which is dependent on the intensity of the radiation received within the cell. The signals thus produced are therefore measures of the attenuation of the x-ray beam by the portion of the body through which it passed.

In operation, x-ray readings are taken from each cell at a plurality of angular positions with respect to the patient, as the source and detector array are rotated about the patient aperture. Each set of readings at a particular angle is often referred to as a projection or view. The projection can be considered to be made up of a number of elements, each element representing one of the detector readings. The readings thus produced for each view are digitized and fed to a reconstruction computer 16 which can use one of a number of available algorithms to produce the image of the cross section traversed by the fan beam. The image can be displayed on a CRT 17, or alternatively can be used to create a film for further study by a diagnostician.

FIG. 1 shows a scanner geometry which has come to be known as rotate-rotate, in which the source is fixed with respect to the detector array, and they rotate in unison about the patient aperture. The invention to be described herein is applicable not only to this geometry, but to other CT geometries as well, the common characteristic being the creation of a plurality of projections made up of a plurality of elements.

Figure 2:
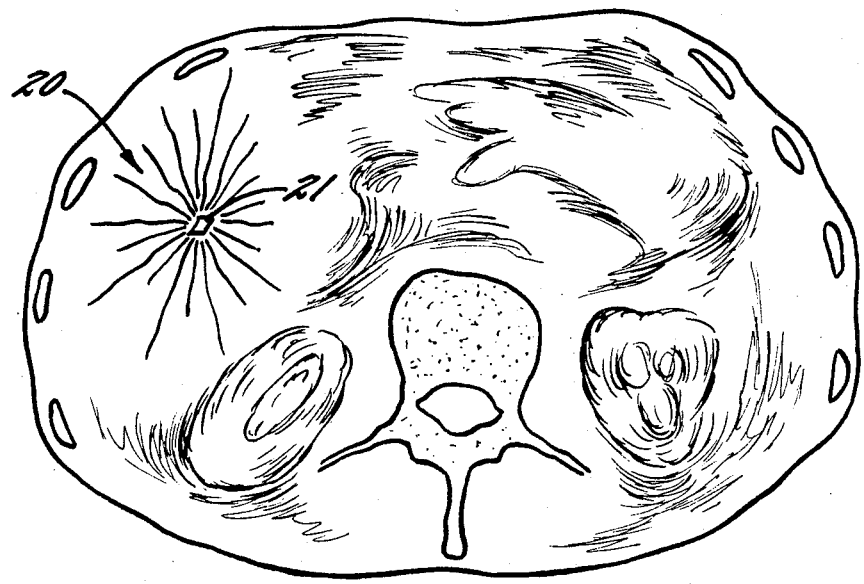
FIG. 2 is a reproduction of a portion of a CT image illustrating a starburst artifact.

Turning to FIG. 2, there is shown a portion of a CT image of the body including a starburst artifact 20 shown emanating from the site of a surgical clip 21. As can be seen, the artifact appears as a series of streaks which emanate radially from the site of the clip.

The streak artifacts may, in principle, be caused by various effects such as undersampling, beam hardening, partial volume effects, detection system nonlinearities due, for example, to underranging of the electronics, or to motion. We have discovered through study and experiment that the artifact illustrated in FIG. 2 is primarily caused by motion. Subtle sudden motion of a high contrast, high density object such as a surgical clip would result in a streak oriented in the direction of the projection being measured at the time of the motion. Movement of even less than a resolution distance is sufficient to cause a significant artifact. Normal metabolic activity can cause involuntary displacement of the metallic clip in rhythm with peristaltic or circulatory functions. If the metal object had a pulsatile motion at the heartbeat rate, one would expect an inconsistency in the scan data set and a streak in the reconstruction at each of those view angles where the object was displaced—of the order of 10 during a 9.8 sec. scan such as that in FIG. 2. Only slight differential motion would be required in order to produce such streaks since the metal object, if faithfully reconstructed, would have a CT number of several thousand H.U. These characteristics are descriptive of the artifact seen in FIG. 2.

In summary, it is believed that motion causes most of the error and the high intensity and sharpness of the shadow created by the surgical clip, in effect a sharp sudden discontinuity, causes the error and the effect on the reconstruction to be appreciable. As will be appreciated from the following description, the present invention eliminates the artifact (as well as the object) whether or not it is caused by motion.

In accordance with the invention, projections which have been "contaminated" by a high density object are rendered consistent by "rubbing out" the contamination from the projection set and using the modified projection set for reconstructing an image with substantially reduced artifacts. Ideally, the rub-out region should be a small percentage of the total field of view so that only a small number of detector positions are involved. The approach is to render the elements or detector readings within the rub-out region consistent (in the Radon sense) with the remaining elements such that the CT image can be reconstructed in the normal way.

Through study and experiment, we have found that acceptable results are not achieved if the projections are handled independently of each other, using only the information within a given projection set to render the elements consistent within the rub-out region. The nature of the problem and the difficulties which we have encountered will be described in connection with FIG. 3.

Figure 3:
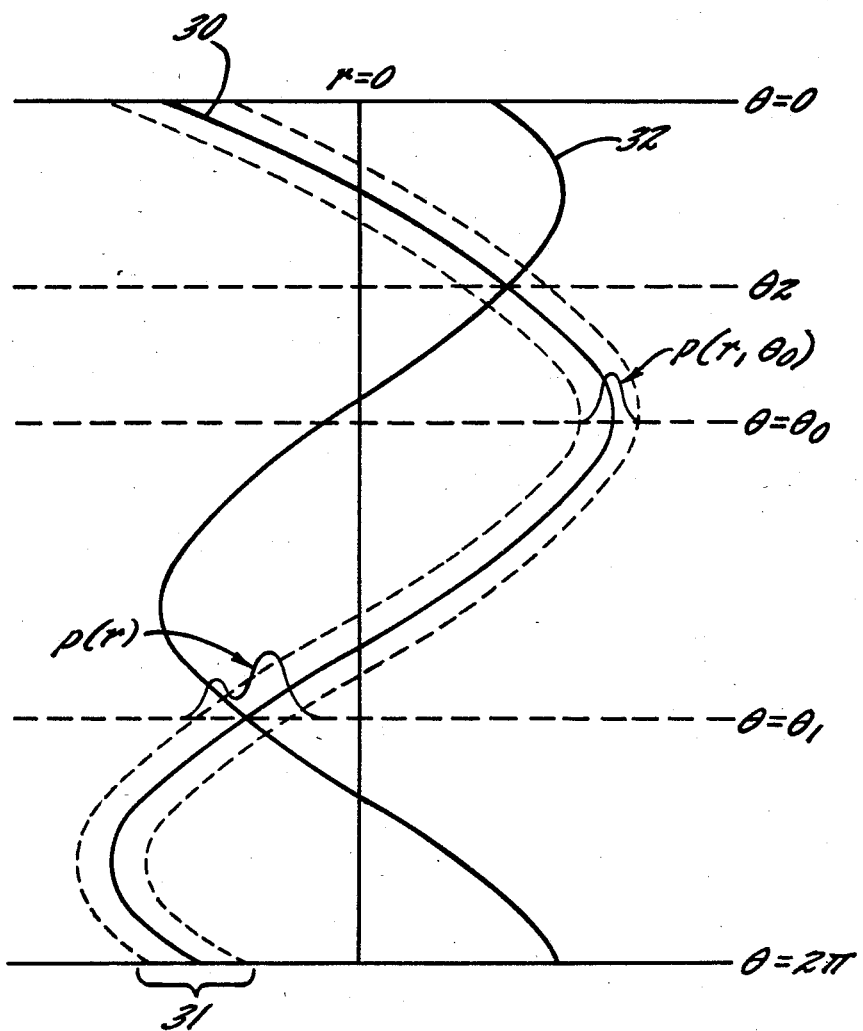
FIGS. 3-7 are diagrams illustrative of CT projection sets and useful in understanding the present invention.

FIG. 3 is a sinogram, which is a plot illustrative of a projection set which can be used for creating a CT image. A sinogram is a display, or in the case of FIG. 3, a partial plot, of detector position on the horizontal axis, view number on the vertical axis, with detector reading or density being denoted by the density (gray scale) at any given point. Thus, any object not in the exact center of the patient aperture will be sensed by different detectors in each view or projection, with the result that the density of that object will appear on the sinogram as an approximately sinusoidal plot caused by the change from detector cell to detector cell as projections are taken during the rotation of the source and detector about the patient aperture.

Turning to FIG. 3, there are illustrated a plurality of projections beginning at $\theta = 0$ and ending with $\theta = 2\pi$, representing projections for a full 360 degree rotation of the source and detector. The centered vertical line $r = 0$ represents the densities sensed by the central detector, with the remaining detectors illustrated to the left and right thereof. The approximately sinusoidal locus illustrated at 30 represents the increased localized density created by an object to be removed, such as a surgical clip. It is seen that the detector positions which sense the clip change with view to describe an approximately sinusoidal locus on the sinogram.

In order to identify the object to be removed, an operator must define a particular area containing the object on an uncorrected CT image. That can be accomplished in modern scanners using a region of interest ROI feature and the CRT display 17 to define an elliptical area encompassing the discontinuity. It is desirable to define the area as small as possible so that a minimum number of detector positions are affected. The effect of defining the rub-out region is illustrated by the dashed area 31 of FIG. 3 which illustrates tne rub-out region containing the object to be removed as defined by the operator.

In accordance with the invention, means are provided to modify (as described below) the elements within the region 31 to remove the effect of the sharp discontinuity within that region. Referring to the angle $\theta = \theta_0$, it is seen that the discontinuity creates a set of detector signals which can be described as $p(r, \theta_0)$ which is sharply peaked by the discontinuity. In the absence of other high density objects within the rub-out area for that projection, it is possible to replace that function by a smooth base line function determined by densities just outside the rub-out region. However, that approach is found to fail in a practical sense because of situations such as that illustrated at the projection $\theta = \theta_1$. At that angle, the discontinuity 30 created by the surgical clip 20 crosses (or is seen through) another highly dense object 32, such as the spinal cord. At that point, the function $p(r, \theta_1)$ is affected not only the high density object which is to be removed, but also by another high density object which it is desired to image. Treating the projection $\theta = \theta_1$ as described in connection with the projection $\theta = \theta_0$ will serve to create another series of artifacts, potentially more troublesome than those being corrected.

In accordance with the invention, we have found that the projection set can be modified to remove the effects of the discontinuity 30 by modifying each projection set in the rub-out region 31 in accordance not only with the particular projection being modified, but also in accordance with neighboring projections. That approach, in effect, takes account of trends in the densities indicated by neighboring views so as to isolate the discontinuity of interest while leaving unaffected the densities which it is desired to image.

As noted above, as a first step in removing an unwanted object from a CT reconstruction, an operator must define the location of the object in an uncorrected image. The location can be anywhere in the CT image. For purposes of removing the object from the reconstruction, it is useful to remap the data set so that the rub-out region is centered in the remapped field of view. Since the projection set can be mapped so that any point in the field becomes the new isocenter, this requirement does not compromise the generality of the method.

Remapping is readily accomplished by translating the elements in each view by an amount $r_0$ which is equal to the negative of the distance from the center of the original projection to the projected center of the rub-out region. Fractional detector translation requires interpolation and it has been found that fifth-order Laplace-Everett interpolation is adequate and nearly as accurate as exact (sinc) interpolation by fast Fourier transforms.

In practicing the invention, the projection set is rendered consistent by using elements not only outside the rub-out region, but also within the rub-out region to estimate the profile to be removed from the elements within the region. Thus, the structures crossing through the rub-out region are taken into consideration in the profile determination and need not be predicted explicitly.

Figure 4:
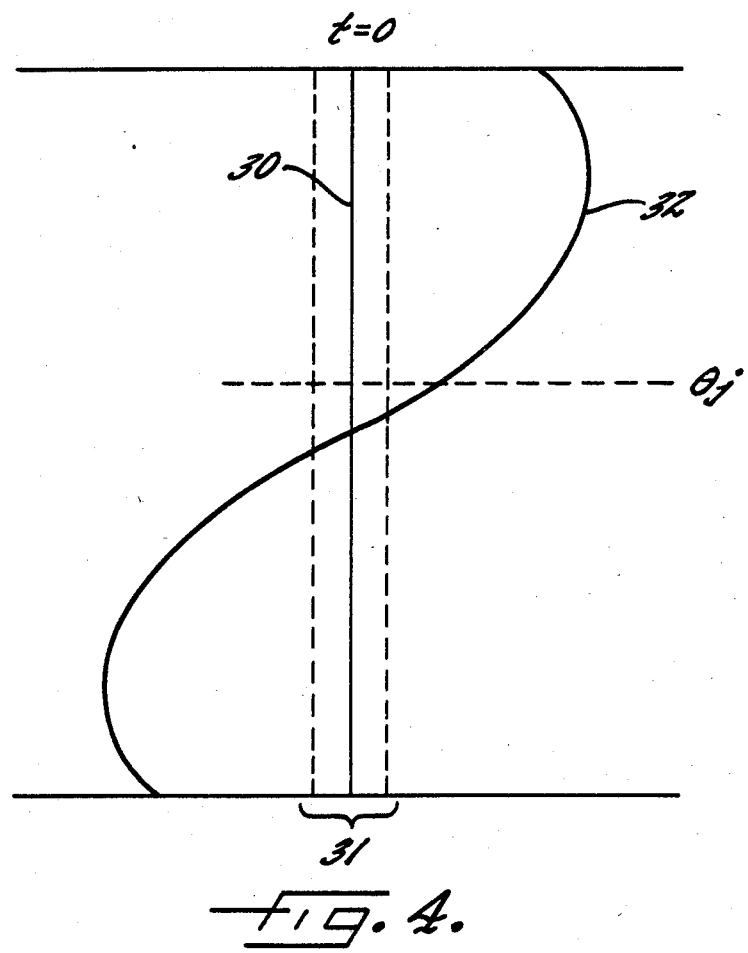

Assume the density of the projection elements are indicated by $p(r_i, \theta_j)$, where r denotes the detector position and $\theta$ denotes the particular projection in question. Referring to FIG. 4, it is seen that the rub-out region 31 has been remapped to assume the isocenter of the projection set with t indicating the position within the remapped set and $t = 0$ indicating the isocenter. The object within the region 31 thus is sensed only by the central detectors of the remapped projection set, and the rub-out region is vertical. The other prominent object 32 of FIG. 3 continues to assume an approximately sinusoidal profile in FIG. 4 since it is not at the center of the remapped projection set.

Figure 5:
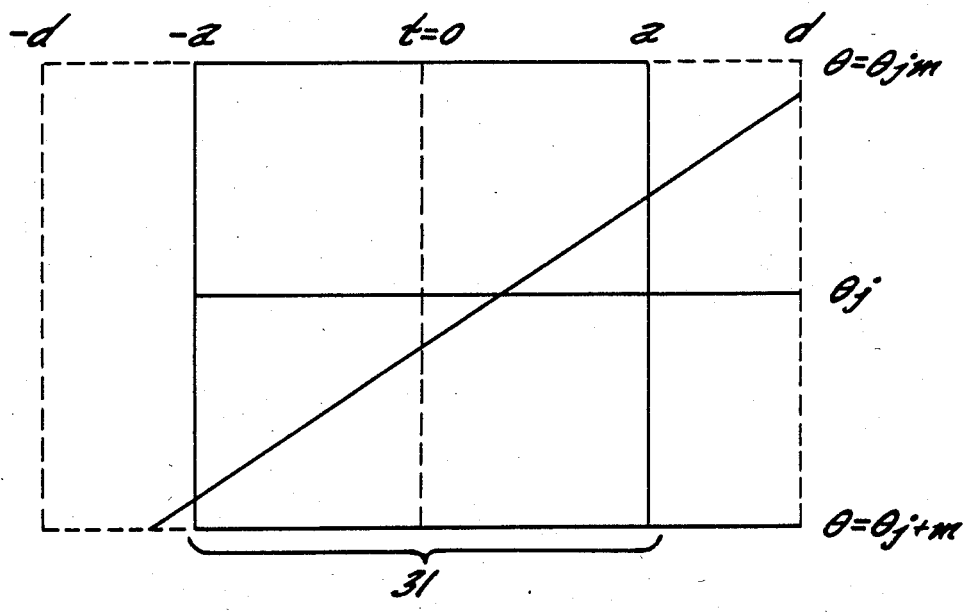

Referring to FIGS. 4 and 5, the manner in which the projection set is modified for some arbitrary projection angle $\theta_j$ will now be described. FIG. 5 shows an enlargement of the rub-out region of the projection set centered about projection $\theta_j$. The rub-out region 31 extends from $-a$ to $+a$, which defines the rub-out region as $|t_i| \leq a$. A second region surrounding the rub-out region is also defined and is used to produce a base line function in defining a rub-out signature for removal of the object. This second region is defined as $a \leq |t_i| \leq d$.

Figure 6:
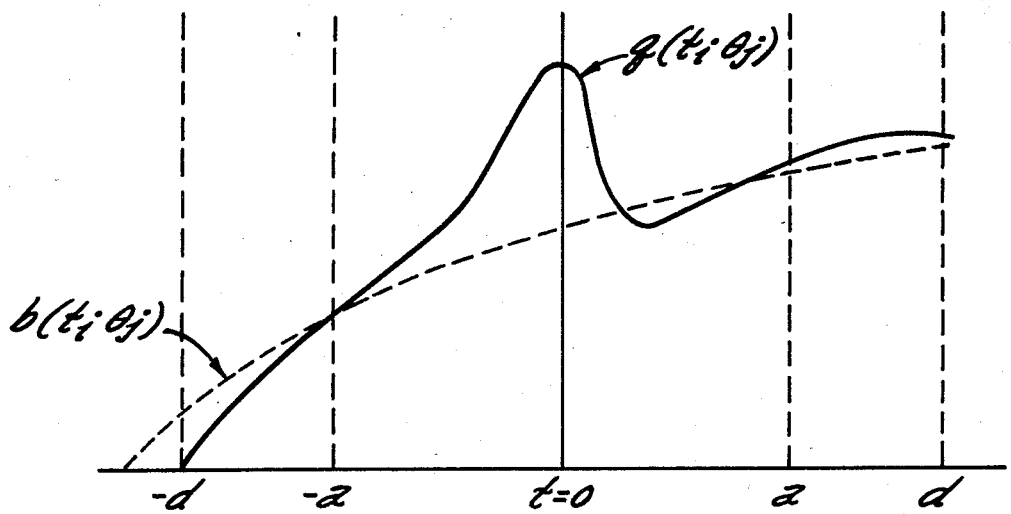

An average function is then defined in both the rub-out region and the second region which depends not only on the elements within the projection $\theta_j$, but also on corresponding elements in M contiguous neighboring projections on each side of the $\theta_j$ projection. The average function $q(t_i, \theta_j)$ is defined as:

$$q(t_i,\theta_j) = \frac{1}{2M+1} \sum_{m=-M}^{M} p'(t_i, \theta_{j+m}), \quad |t_i| < d,$$

and the indices are defined above, where $p'(t_i, \theta_j)$ is the remapped projection at $\theta_j$. The average function $q(t)$ for the projection $\theta_j$ is illustrated in FIG. 6.

It is important to note that, except for edge effects, structures crossing through the rub-out region produce only a smooth base line to $q(t_i, \theta_j)$. This can be appreciated from FIG. 4 which demonstrates that the object within the region 31 will add inherently in the average $q(t_i, \theta_j)$, whereas an object such as 32 will add approximately the same amount at all values of t and thus will contribute a smooth baseline to q.

Having defined an average function which is strongly influenced by the object to be removed, it is then necessary to define a base line function which characterizes the contribution of objects outside the rub-out region such as 32 in FIG. 4. This is accomplished by deriving by least squares regression from the region $a \leq |t_i| \leq d$ a base line function $b(t_i, \theta_j)$. This is accomplished by known statistical techniques which minimize the error between the known information in the projection set and the base line function.

With the average function strongly affected by the discontinuity and the base line function approximating the surround, it is then possible to define a rub-out signature $\delta(t_i, \theta_j)$ which characterizes the discontinuity:

$$\delta(t_i, \theta_j) = q(t_i, \theta_j) - b(t_i, \theta_j), \quad |t_i| \leq a.$$

Figure 7:
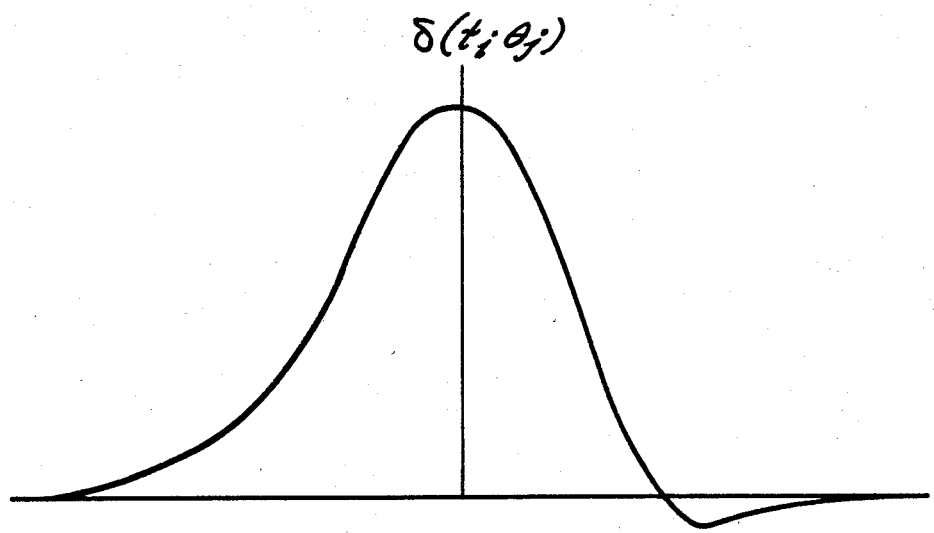

The average function $q(T_i, \theta_j)$ and base line function in the areas in question are illustrated in FIG. 6, and the rub-out signature $\delta(t, \theta_j)$ is illustrated in FIG. 7. This rub-out signature is then remapped into the original projection set by translating a distance $-r_0$ and subtracting the rub-out signature from the original untranslated projection to obtain a new projection $\bar{p}$:

$$\bar{p}(r_i, \theta_j) = p(r_i, \theta_j) - \delta(r_i - r_o, \theta_j)$$

Some smoothing of the correction function near the edges of the rub-out region $|t_i| = a$ has been found useful. The above procedure is repeated for each view in the projection set to produce a modified projection set in which the rub-out signature for each view has been used to remove the effect of the unwanted object. That projection set is then operated on by reconstruction programs long in use for producing a CT image, but one where artifacts from the localized discontinuity are minimized.

The method according to the present invention is broadly illustrated by the steps set out in FIG. 8. First of all, a projection set is created at 40 by exposing the object to be examined with radiation and sensing the radiation at numerous detector positions within each projection and at numerous projection angles. The operator then defines the rub-out region at 41, such as by using the aforementioned region of interest feature.

The projection set is then remapped at 42 to place the rub-out region at the isocenter of the remapped projection set. It is then necessary to select a first projection at 43, and having done that to define at 44 an average function q(t) for that projection within the rub-out region and a small contiguous region using the projection in question as well as M neighboring projections. Having defined the average function for that projection, it is then necessary to use that information at 45 to define a base line function indicating what the rub-out region would have been like had the object in question not been present.

With those steps accomplished, it is then possible to define a rub-out signature $\delta(t)$ from the average function and base line function in step 46. The projection number is then incremented by 1 at 47 thus incrementing the projection angle by the angular increment $\Delta\theta$, and the steps 44–46 repeated for each projection.

After a rub-out signature has been created for each projection in the set, those rub-out signatures are then remapped into the original geometry and are subtracted from the original projection set at step 48. The so-modified projection set thus has the information which had been caused by the sharp discontinuity removed. It is then possible using conventional techniques to reconstruct the image at step 49 to produce an image with artifacts minimized.

The computational steps of the above method can be performed in readily available digital computers. The preferred embodiment of such computer is the Data General Eclipse S200 operating in conjunction with a Floating Point Systems AP-120B array processor.

In addition to the method aspects, the present invention also encompasses computational processor apparatus and includes means for creating a projection set including a source of radiation 10, 40 and a detector array 14, 40. Means 16, 41 are provided for defining a rub-out region containing the object to be removed from the image. In addition, means 16, 44 are provided which are operative on the elements within the rub-out region in each projection for averaging those elements with associated elements from neighboring projections to produce an average function which is strongly influenced by the discontinuity created by the object to be removed. Means, 16, 45–48 are then provided for modifying the original projection set in accordance with the average function to eliminate the discontinuity, and for producing from the so-modified projection set a CT image.

Thus, and in accordance with the invention, it is possible not only to remove inconsistencies from a CT projection set, but also to actually remove the image of the object which created those inconsistencies. The invention finds the application not only in removing the effect of metal surgical clips and the streaks often associated with them, but also to removing the effect of other sharp localized discontinuities, such as dental fillings and the like. Removal of an object as used herein, clearly refers to removal of a portion of a CT image, and thus also encompasses removal of a portion of an object.

We claim as our invention:
1. A method of removing an object from a CT image comprising the steps of exposing a body to radiation at a plurality of angles about the body, detecting radiation passing through the body at the plurality of angles to create a projection set made up of a plurality of projections each made up of a plurality of elements, defining in an unmodified projection set a rub-out region encompassing the object to be removed, operating on the elements in the projection set to determine average densities for each element of each projection within the rub-out region and slightly beyond by combining associated elements from neighboring projections, estimating from the average densities just outside the rub-out region what the densities within the rub-out region would have been if the object were not present, combining the estimate and the average densities to create a rub-out signature, producing a modified projection set by combining the rub-out signature with the original projection set to remove the signature, and producing a corrected image from the modified projection set.

2. A method of removing an object from a CT image comprising the steps of
   exposing a body to radiation at a plurality of angles about the body,
   detecting radiation passing through the body at the plurality of angles to create a set of projections each projection being made up of a plurality of elements,
   defining in an unmodified projection set a rub-out region encompassing the object to be removed,
   operating on the elements in the projection set to estimate the density of the object to be removed by combining associated elements from a plurality or nighboring projections within the rub-out region,
   modifying the densities within the rub-out region by eliminating the estimated density therefrom, and
   utilizing the modified densities to produce and display a corrected CT image.

3. A method of removing an object from a CT image comprising the steps of
   exposing a body to radiation at a plurality of angles about the body,
   detecting radiation passing through the body at the plurality of angles to create a set of projections each projection being made up of a plurality of elements,
   defining in an unmodified projection set a rub-out region encompassing the object to be removed,
   for each element in each projection within the rub-out region, combining that element with associated elements from neighboring views to define an average within the rub-out regio in which the elements therein are influenced by corresponding elements in neighboring views,
   producing a rub-out signature for each view from said average,
   remapping the rub-out signatures into the orignal projection set,
   and producing and displaying a corrected image from the projection set with rub-out signatures remapped thereinto.

4. A method of removing an object from a CT image comprising the steps of
   exposing a body to radiation at a plurality of angles about the body,
   detectig radiation passing through the body at the plurality of angles to create a set of projections each projection being made up of a plurality of elements,
   defining in an unmodified projection set a rub-out region encompassing object to be removed,
   reordering the elements in the projection to place the rub-out region at the isocenter of the set of projections.
   defining in an unmodified projection set a second region encompassing the rub-out region in each projection,
   for each element in each projection within the rub-out and second regions, combining elements from a plurality of neighboring views to define an average function strongly affected by the object to be removed,
   for each projection, combining elements from the second region but not from the rub-out region to produce a base line function for the rub-out region,
   combining the base line and average functions to produce a rub-out signature for each view,
   remapping the rub-out signature into the original projection set to produce a modified projection set with said object removed, and
   producing and displaying a corrected CT image from the modified projection set.

5. A CT scanner for producing images with objects creating sharp discontinuities selectively removable therefrom comprising, in combination,
   a source of radiation for exposing an image field from a plurality of angles,
   detector means for detecting the radiation to create a plurality of projections each comprised of a plurality of elements, said plurality of projections defining a projection set and
   computational processor means including:
   means for defining in an unmodified projection set a rub-out region containing the object to be removed from the image,
   means operative on the elements within the rub-out region and operative on each projection for averaging the elements with associated elements from neighboring projections to produce an average function strongly influenced by the discontinuity crated by the object to be removed,
   means for modifying the original projection set in accordance with the average function to eliminate the effect of the discontinuity from the projection set, and
   means for producing a corrected CT image from the modified projection set.

* * * * *

UNITED STATES PATENT AND TRADEMARK OFFICE
CERTIFICATE OF CORRECTION

PATENT NO.   :   4,590,558
DATED        :   May 20, 1986
INVENTOR(S)  :   Gary H. Glover and Norbert J. Pelc It is certified that error appears in the above-identified patent and that said Letters Patent is hereby corrected as shown below:

Column 5, line 44, after "function", second occurrence, insert -- $b(t_i, \theta_j)$ --.

Claim 2, column 7, line 31, change "or" to -- of --;

Claim 2, column 7, line 32, change "nighboring" to -- neighboring --.

Claim 3, column 7, line 50, change "regio" to -- region --.

Signed and Sealed this

Twenty-sixth Day of August 1986

[SEAL]

Attest:

DONALD J. QUIGG

Attesting Officer          Commissioner of Patents and Trademarks